United States Patent
Carey et al.

(10) Patent No.: US 9,421,124 B2
(45) Date of Patent: Aug. 23, 2016

(54) SYSTEMS FOR APPLYING HEAT AND PRESSURE TO SINUSES

(76) Inventors: Michelle E. Carey, Lake Stevens, WA (US); Angela T. M. Hays, Idaho Falls, WA (US)

( * ) Notice: Subject to any disclaimer, the term of this patent is extended or adjusted under 35 U.S.C. 154(b) by 1133 days.

(21) Appl. No.: 13/410,738

(22) Filed: Mar. 2, 2012

(65) Prior Publication Data
US 2012/0222192 A1 Sep. 6, 2012

Related U.S. Application Data

(60) Provisional application No. 61/448,275, filed on Mar. 2, 2011.

(51) Int. Cl.
*A61F 7/02* (2006.01)
*A61F 7/00* (2006.01)

(52) U.S. Cl.
CPC .......... *A61F 7/02* (2013.01); *A61F 2007/0004* (2013.01); *A61F 2007/0071* (2013.01); *A61F 2007/0078* (2013.01); *A61F 2007/0086* (2013.01); *A61F 2007/0096* (2013.01); *A61F 2007/0255* (2013.01); *A61H 2201/0228* (2013.01); *A61H 2201/1607* (2013.01); *A61H 2201/5015* (2013.01); *A61H 2205/025* (2013.01)

(58) Field of Classification Search
CPC combination set(s) only.
See application file for complete search history.

(56) References Cited

U.S. PATENT DOCUMENTS

| | | | |
|---|---|---|---|
| 4,186,294 A * | 1/1980 | Bender | 219/527 |
| 4,570,635 A * | 2/1986 | Henig | 607/109 |
| 2002/0019654 A1* | 2/2002 | Ellis et al. | 607/98 |
| 2006/0224091 A1* | 10/2006 | Boys | 601/78 |
| 2006/0235494 A1* | 10/2006 | Vanderschuit | 607/89 |
| 2007/0016271 A1* | 1/2007 | Hammond | 607/96 |
| 2009/0054959 A1* | 2/2009 | Felker | 607/111 |

* cited by examiner

*Primary Examiner* — Joseph Stoklosa
*Assistant Examiner* — Adam Avigan
(74) *Attorney, Agent, or Firm* — Michelle E. Carey; Telekta Law, P.S.

(57) ABSTRACT

An eye mask with an internal heating mechanism worn over the eye and sinus regions of the wearer. The eye mask provides heat and pressure to the face. A plurality of heating wires internal to the mask provide heat, the heating wires being driven by temperature and time controls contained in an external enclosure that may also contain batteries or other connections to a power source. The mask may have pockets for weighted pebbles, magnets or other material for adding weight to the mask to bring the heat closer to the face of the wearer. The mask may have a reflective material in an internal layer to reflect heat from the heating wires back to the face of the wearer. The mask may have a memory foam for molding the mask to the contours of the face, bringing heat to a greater portion of the face of the wearer.

19 Claims, 6 Drawing Sheets

SYSTEMS FOR APPLYING HEAT AND PRESSURE TO SINUSES

PRIORITY CLAIM

This invention claims the benefit of U.S. provisional patent application Ser. No. 61/448,275 filed Mar. 2, 2011 (our ref. CARE-1-1001). The foregoing application is incorporated by reference in its entirety as if fully set forth herein.

FIELD OF THE INVENTION

This invention relates generally to heating, and more specifically, to systems for applying heat and pressure to sinuses.

SUMMARY

This invention relates generally to heating, and more specifically, to systems for applying heat and pressure to sinuses. In some embodiments, a system for applying heat and pressure to sinuses may include an eye mask which covers a portion of the face of the wearer, including the eyes and sinus regions. The eye mask may be configured with heating wires inside the mask, the heating wires being controlled in some embodiments by a temperature control circuit driven by temperature and duration inputs and a plurality of temperature sensors inside the mask to enable thermostatic control.

In some embodiments, the eye mask may have weights for holding the mask against the face of the wearer. The eye mask may also have an infrared reflective layer for trapping heat and redirecting it to the face of the wearer. The eye mask may also have a thermoreactive memory foam layer for molding the mask to the contours of the face of the wearer and providing heat to a greater portion of the face of the wearer.

In some embodiments, the eye mask has a control enclosure which may have batteries for powering the eye mask. In some embodiments, the control enclosure may be connected to a wall charger or other connection to external power.

BRIEF DESCRIPTION OF THE DRAWINGS

Embodiments of the present invention are described in detail below with reference to the following drawings.

DETAILED DESCRIPTION

This invention relates generally to heating, and more specifically, to systems for applying heat and pressure to sinuses. Specific details of certain embodiments of the invention are set forth in the following description and FIGS. 1-5 to provide a thorough understanding of such embodiments. The present invention may have additional embodiments, may be practiced without one or more of the details described for any particular described embodiment, or may have any detail described for one particular embodiment practiced with any other detail described for another embodiment.

Figure 1A:
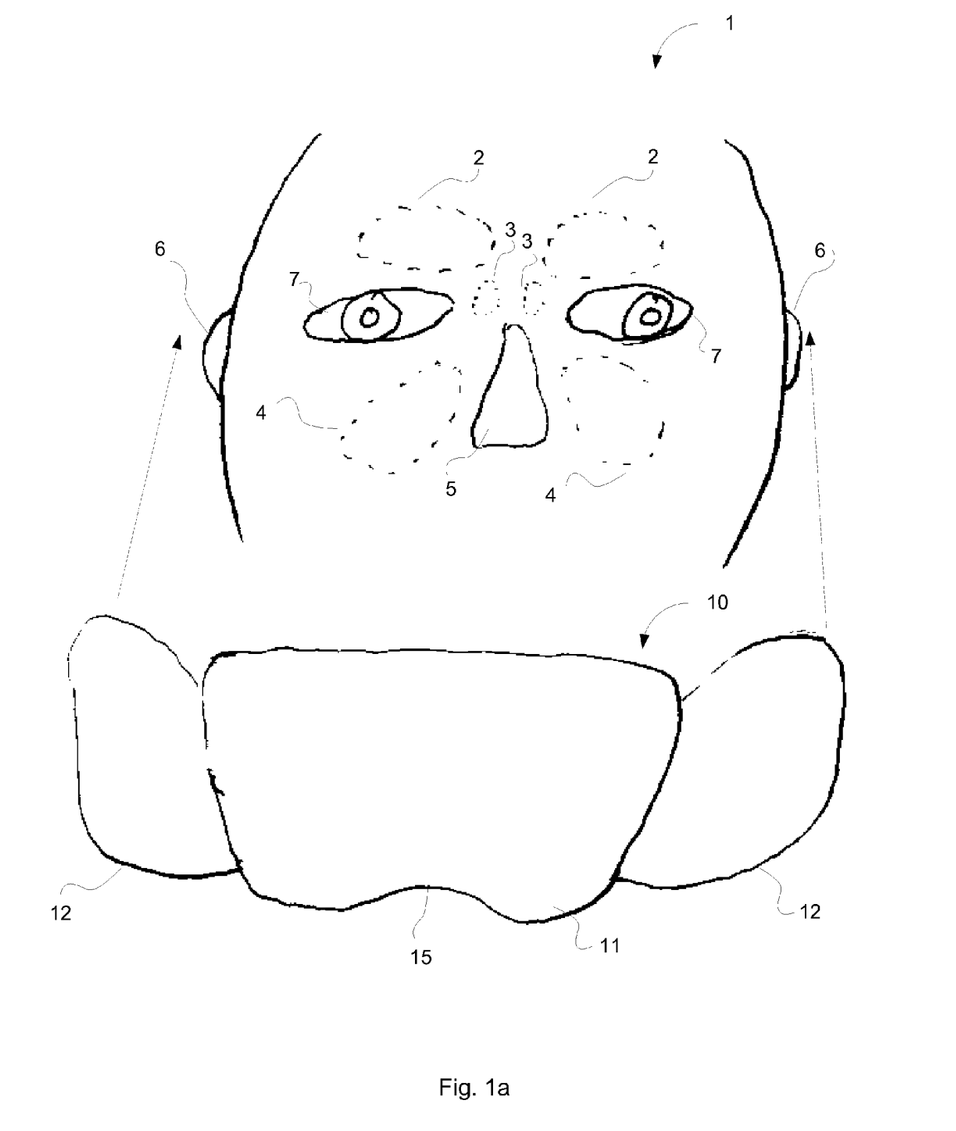
FIGS. 1a and 1b are a front view and a side view of a system for applying heat and pressure to sinuses, in accordance with an embodiment of the invention.
Figure 1B:
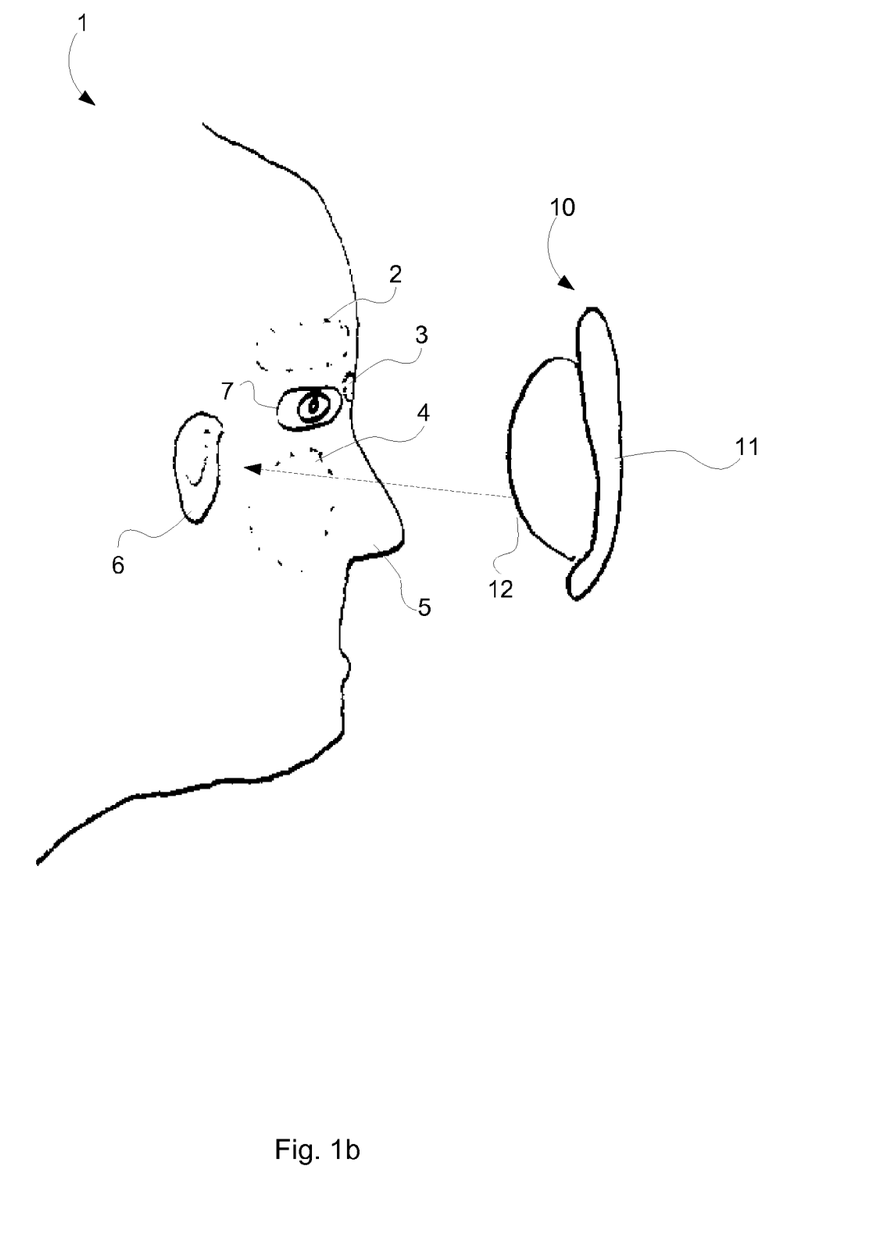

FIGS. 1a and 1b are a front view and a side view of a system for applying heat and pressure to sinuses, in accordance with an embodiment of the invention. In some embodiments, an eye mask 10 may be worn by a wearer 1, the wearer desiring to provide heat and pressure over the eyes 7 of the wearer and to the sinus regions 2, 3 and 4 of the wearer. The sinus regions 2, 3 and 4 of the wearer 1 may include the frontal sinus regions 2, the ethmoid and sphenoid sinus regions 3 and the maxillary sinus regions 4.

In some embodiments, an eye mask 10 has a front panel 11. In some embodiments, an eye mask 10 may have elastic straps 12, the elastic straps configured to hook behind the ears 6 of the wearer 1. In different embodiments, an eye mask 10 may have other structures for permitting the eye mask to rest on the face of the wearer 1. For example, in some embodiments, an eye mask 10 may have one or more cloth straps. In some embodiments, there may be a cloth strap attached to either side of the eye mask 10 proximate to the temples of the wearer, where the cloth straps have a hook-and-loop style fastener which mates the cloth straps together behind the head of the wearer 1. In different embodiments, the one or more cloth straps may have different fasteners such as snaps, adjustable buckles, or other such designs to permit adjustment of the eye mask 10 to be comfortably worn over different sized heads. In some embodiments, the straps are not cloth but are made of a different material. In another embodiment, the eye mask 10 may have a single elastic strap, the single elastic strap being attached to each of the left and right side of the mask proximate to the temples of the wearer, where the single elastic strap goes around the head of the wearer. In some embodiments, the single elastic strap is adjustable for size. In different embodiments, the eye mask 10 has no structure for retaining the mask over the face of the wearer 1, where the wearer lies prone with the mask over the top of the face such that the mask stays in place solely with gravity. In different embodiments, the eye mask 10 is incorporated into a full-head garment such as a ski-mask.

In some embodiments, the front panel 11 of the eye mask 10 covers the eyes 7 of the wearer 1, preventing light from reaching the eyes of the wearer. In some embodiments, the front panel 11 of the eye mask 10 includes decorative fabric, such as sateen or flannel. In some embodiments, the eye mask 10 has a recess 15 at the bottom edge of the mask configured for permitting air to reach the nose 5 of the wearer 1.

Figure 2:
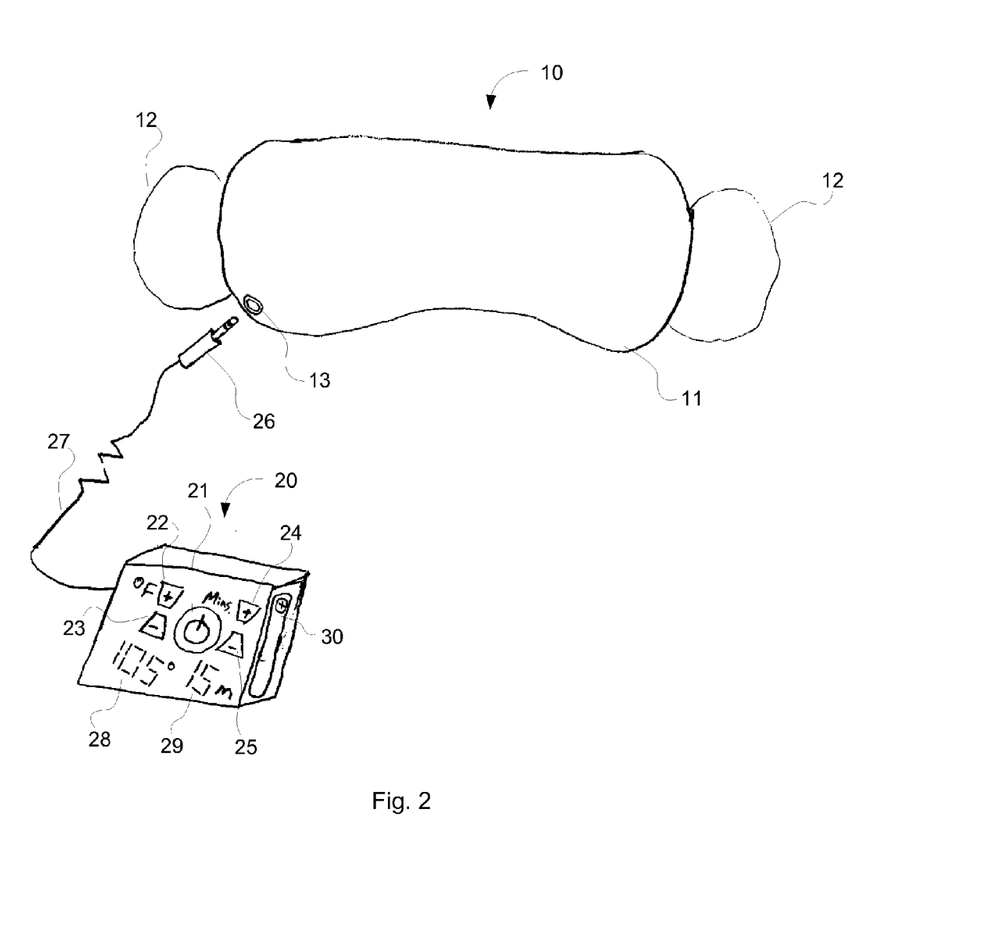
FIG. 2 is a front view of a system for applying heat and pressure to sinuses, in accordance with an embodiment of the invention.

FIG. 2 is a front view of a system for applying heat and pressure to sinuses, in accordance with an embodiment of the invention. In some embodiments, an eye mask 10 may have an external control enclosure 20, the external control enclosure housing a power source and/or controls. In some embodiments, the external control enclosure 20 may connect to the eye mask 10 via a cord 27, a plug 26 and a jack 13. It will be recognized by those with skill in the art that a connection between a control enclosure 20 and the eye mask 10 may be removable or permanently hard-wired, and that the plug and jack may take any form including where a plug and jack connection is made at either the eye mask 10 or the control enclosure 20 or both. It will be further recognized by those with skill in the art that many plug and jack combinations exist, such as a barrel connector, USB, mini-USB, micro-USB, serial port, magnetic contact, inductive contacts or any other structure for making a signal and/or electric connection between a mask and control enclosure, and the instant disclosure is non-limiting as to this structure. In some embodiments, the power source is internal to the eye mask 10. In some embodiments, the controls for the eye mask 10 are located on an external surface of the eye mask 10. In different embodiments, the power source and the controls for the eye mask 10 are in different enclosures. In different embodiments, only a power source is needed and no control is provided, such that when power is available the mask operates.

In some embodiments, a control enclosure 20 may include an internal power source with a battery door 30 providing access to the internal power source. In some embodiments, an internal power source is comprised of standard-sized batteries, such as one or more readily-available AA, AAA, 9V or other standard-sized battery. In some embodiments, an internal power source is comprised of flat batteries or other nonstandard-sized batteries designed to fit the enclosure and not be replaced.

In some embodiments, an internal power source is comprised of disposable batteries, such as an alkaline battery. In different embodiments, an internal power source is a rechargeable battery, such as a Ni-Cad or L-Ion battery. In some embodiments, recharging of rechargeable batteries is done externally to the control enclosure 20 using a recharger (not shown). In different embodiments, recharging of the rechargeable batteries is done using an external charger that plugs into the control enclosure 20 (seen in FIG. 5).

In some embodiments, the control enclosure 20, having internal disposable or rechargeable batteries, is an attached portable battery pack. In different embodiments, a control enclosure 20 may connect directly to household power, where the household power is an alternating current or direct current connection. In different embodiments, a control enclosure 20 may connect to a DC adapter, the DC adapter configured for receiving auto power (as in, for example, a cigarette lighter adapter in a car or a 12V power connector in an airplane).

In some embodiments, power is carried to the eye mask 10 from the power source in the control enclosure 20 via the cord 27, the plug 26 and the jack 13.

In some embodiments, a control enclosure 20 may have controls for setting a temperature of the heat to be directed to the face of the wearer. Such controls may be, for example, a temperature up button 22, a temperature down button 23 and a temperature display 28. It will be recognized by those with skill in the art that many structures for setting a temperature exist and all such structures may be included within the scope of the present invention. For example, setting of temperature may be accomplished via a rotary dial, a slider switch, a touch screen or a plurality of buttons where different buttons result in different temperatures. In some embodiments, a temperature adjustment control is not provided, with a single temperature being factory-set.

In some embodiments, a control enclosure 20 may have controls for setting a duration during which heat should be directed to the face of the wearer. Such controls may be, for example, a time up button 24, a time down button 25 and a time display 29. It will be recognized by those with skill in the art that many structures for setting a duration exist and all such structures may be included within the scope of the present invention. For example, setting a duration may be accomplished via a rotary dial, a slider switch, a touch screen or a plurality of buttons where different buttons result in different durations. In some embodiments, a duration control is not provided, with a single duration being factory-set, or with the duration being controlled strictly by an on/off button.

In some embodiments, a control enclosure 20 may have an on/off button 21. It will be recognized by those with skill in the art that many structures for providing an on/off function exist, including many of the examples provided above with respect to a temperature setting, and all such structures may be included within the scope of the present invention. In some embodiments, an on/off button is not present, with the eye mask 10 operable whenever power is being provided to the mask through connection to a power source.

Figure 3A:
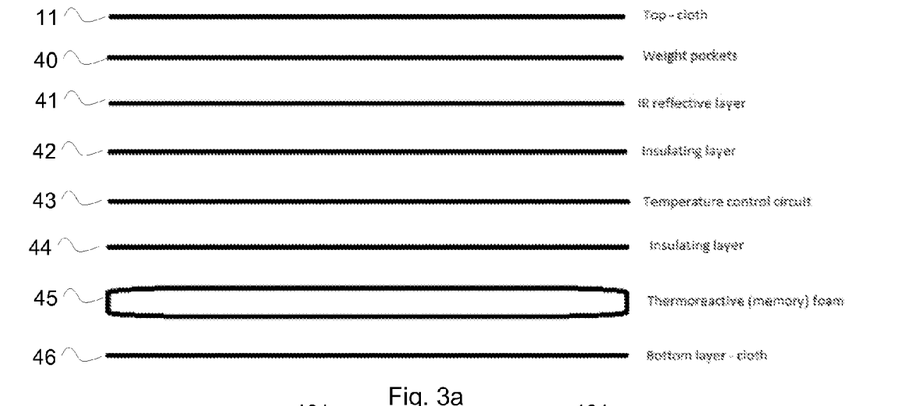
FIG. 3a is an exploded view of a system for applying heat and pressure to sinuses, in accordance with an embodiment of the invention.
Figure 3B:
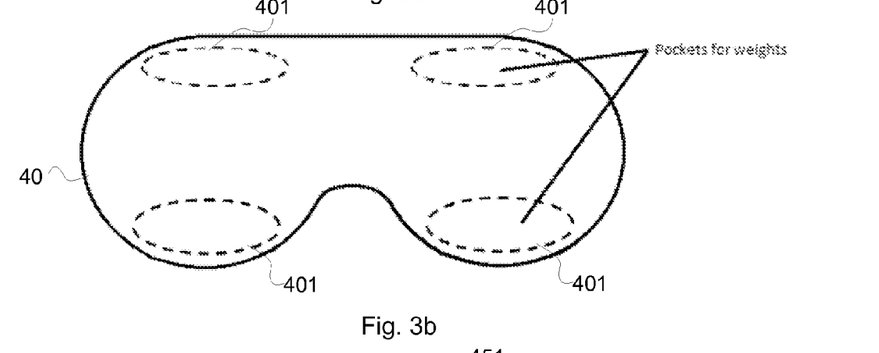
FIGS. 3b and 3c are front cross-sectional views of a system for applying heat and pressure to sinuses, in accordance with an embodiment of the invention.

FIG. 3a is an exploded view of a system for applying heat and pressure to sinuses, in accordance with an embodiment of the invention. In some embodiments, an eye mask may be comprised of a plurality of layers. In some embodiments, the plurality of layers may include a front panel 11, a weight pocket layer 40, an IR reflective layer 41, an outer insulating layer 42, a temperature control circuit layer 43, an inner insulating layer 44, a thermoreactive foam layer 45 and a bottom layer 46. In some embodiments, the layers are stitched or otherwise affixed together so that the plurality of layers forms a single mask. In different embodiments, some layers may be affixed by hook-and-loop or other non-permanent fasteners in order to be temporarily removed.

In some embodiments, the front panel 11 of the eye mask 10 covers the eyes 7 of the wearer 1, preventing light from reaching the eyes of the wearer. In some embodiments, the front panel 11 of the eye mask 10 includes decorative fabric, such as sateen or flannel. In some embodiments, a front layer 11 is stitched to the rest of the layers. In different embodiments, a front layer 11 is affixed to the rest of the layers with hook-and-loop or other non-permanent fasteners such that it may be temporarily removed from the eye mask 10.

In some embodiments, a weight pocket layer 40 of the eye mask 10 is provided. As can be seen more clearly in FIG. 3b, a weight pocket layer 40 has at least a portion of the layer configured for receiving weights. In some embodiments, the weights are retained within a plurality of pockets 401, the plurality of pockets 401 located at the corners of the mask, weighting the mask to hold the mask and its heat substantially near the sinus regions of the wearer, enabling the mask to provide pressure. In some embodiments, the plurality of pockets 401 hold pebbles or other weights. In some embodiments, the plurality of pockets 401 hold magnets, which the wearer may understand to stimulate blood flow through the sinus regions. In some embodiments the plurality of pockets 401 are user-accessible (being accessed, for example, by temporarily removing the front layer 11 as previously disclosed), enabling the wearer to add or remove weight to the pockets.

Returning to FIG. 3a, in some embodiments, an eye mask 10 may include an IR reflective layer 41, the IR reflective layer configured for reflecting heat emanating from the temperature control circuit layer 43 back towards the bottom of the eye mask and to the face of the wearer 1. In some embodiments, the IR reflective layer 41 is constructed of BoPET (Biaxially-oriented polyethylene terephthalate) polyester film, aluminum foil or other material configured to reflect heat.

In some embodiments, an eye mask 10 may include a temperature control circuit layer 43, the temperature control circuit layer being surrounded by insulating layers, including an outer insulating layer 42 and an inner insulating layer 44. The temperature control circuit layer 43 is an electrically-generated heat source and will be further discussed with respect to FIG. 4. The insulating layers 42 and 44 electrically insulate the electrical circuitry contained within the temperature control circuit layer 43. In some embodiments, the insulating layers are constructed of flexible plastic, cloth, or other electrically-insulating material designed to contain the electrical circuitry of the temperature control circuit layer 43. In some embodiments, the outer insulating layer 42 (the outer insulating layer being closest to the front panel 11) may be further configured for retaining heat. In some embodiments, the temperature control circuit layer 43 is completely electrically insulated such that the insulating layers 42 and 44 are not needed.

Figure 3C:
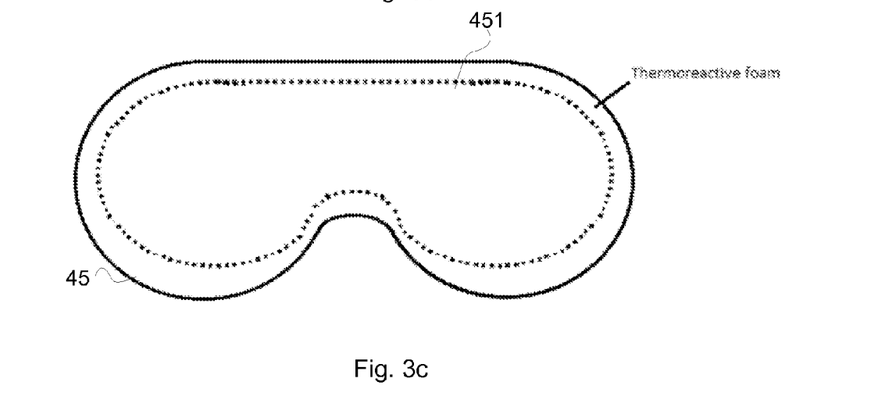

As can be seen in FIG. 3c, in some embodiments, an eye mask 10 may include a thermoreactive foam layer 45, the thermoreactive foam layer configured for bending to a certain shape. A thermoreactive foam layer may be "memory foam" such that it retains the shape into which it is bent. In this way, an eye mask 10 may mold to the contours of the face of the wearer 1, providing heat and pressure to a greater portion of the face of the wearer. Such memory foam may be, for example, 3 Lb ViscoSaver memory foam, available from commercially available sources, such as Foam Factory, Inc., on the web at foamdistributing.com.

Returning to FIG. 3a, in some embodiments, an eye mask 10 may include a bottom layer 46. In some embodiments, the bottom layer 46 of the eye mask 10 includes decorative fabric, such as sateen or flannel. The bottom layer 46 comes into contact with the face of the wearer 1 and may alternatively be constructed of other soft material such as satin, jersey, breathable cotton or other suitable fabric. In some embodiments, a bottom layer 46 is stitched to the rest of the layers. In different embodiments, a bottom layer 46 is affixed to the rest of the layers with hook-and-loop or other non-permanent fasteners such that it may be temporarily removed from the eye mask 10. In some embodiments, further layers comprise a removable cover that at least partially envelopes the eye mask 10.

Figure 4:
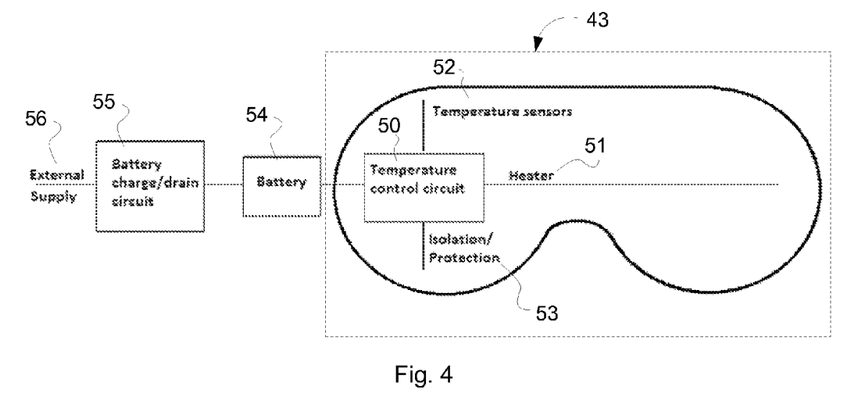
FIG. 4 is a block diagram of a system for applying heat and pressure to sinuses, in accordance with an embodiment of the invention.

FIG. 4 is a block diagram of a system for applying heat and pressure to sinuses, in accordance with an embodiment of the invention. In some embodiments, a system for applying heat and pressure to sinuses includes a temperature control circuit layer 43, the temperature control circuit layer being powered by a power source which may be a battery 54 (the battery 54 being discussed previously related to FIG. 2), the battery perhaps being rechargeable and requiring a battery charge/drain circuit 55 and an external power supply 56. As previously disclosed, the system may have disposable batteries and not be provided with an external power supply or battery charging circuit, or the system may be powered strictly from household or vehicle power not requiring a battery or battery charge/drain circuit but still including an external power cord or power supply such as a wall charger.

In some embodiments, the temperature control circuit layer 43 may include a heater 51. In some embodiments, the heater 51 is a plurality of heating wires distributed through the temperature control circuit layer, the operation and temperature of the heating wires being controlled by a temperature control circuit 50. In some embodiments, the temperature control circuit layer 43 may include a plurality of temperature sensors 52 distributed through the temperature control circuit layer, the temperature sensors providing input to the temperature control circuit 50 so that the control circuit may thermostatically control power to the heating wires (i.e. if the temperature sensors sense a temperature greater than that set on the control enclosure, the control circuit reduces or removes power to the heating wires). The temperature control circuit 50 may also receive input corresponding to the duration set on the control enclosure and operating the heating wires accordingly (i.e. providing power to the heating wires only until the end of a duration set on the control enclosure). The temperature control circuit 50 may also receive input corresponding to the on/off switch on the control enclosure and operate the heating wires accordingly. In some embodiments, the temperature control circuit layer 43 may include circuitry for isolation/protection 53, which may provide overload protection, ground fault protection, fuse-like protection or any other electrical safety measures designed to prevent electrical malfunction or injury.

Figure 5:
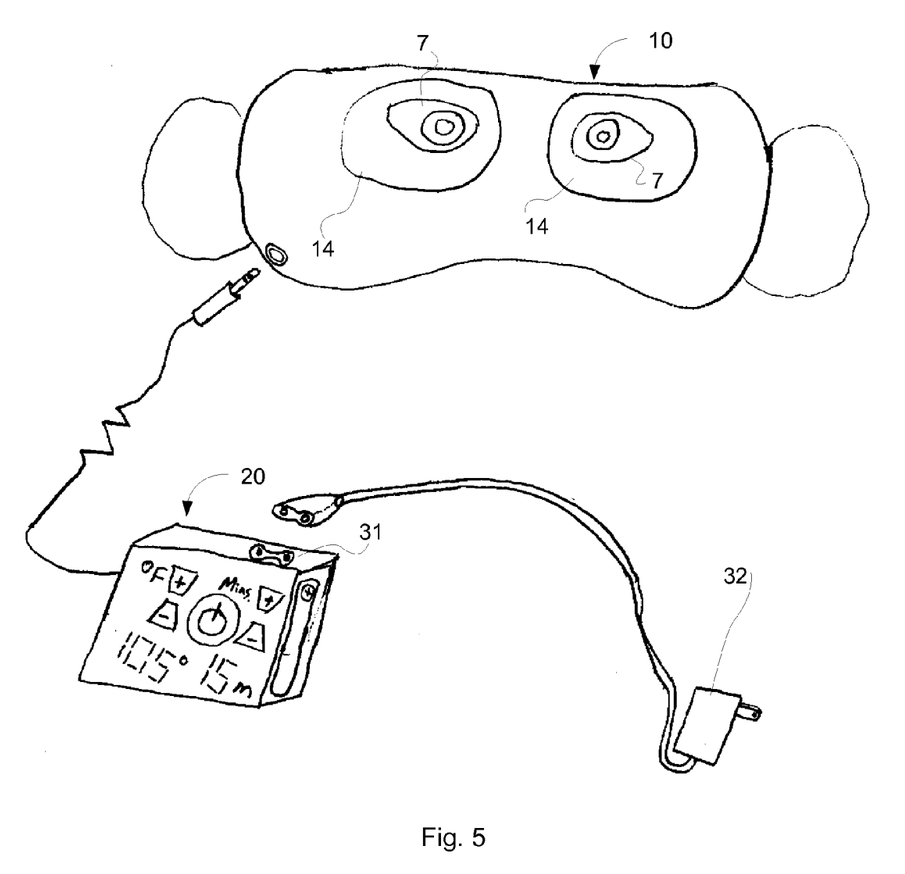
FIG. 5 is a front view of an alternate embodiment of a system for applying heat and pressure to sinuses, in accordance with an embodiment of the invention.

FIG. 5 is a front view of an alternate embodiment of a system for applying heat and pressure to sinuses, in accordance with an embodiment of the invention. In some embodiments, an eye mask 10 may have apertures 14 disposed through all the layers configured for exposing the eyes 7 of the wearer, so that the wearer can still see while wearing the eye mask. In different embodiments, the eye mask 10 may have flaps or other closures (flaps or other closures not shown) which may fasten with hook-and-loop fasteners that permit the wearer to temporarily expose the eyes 7 and then close the flaps. In other embodiments, the layers may be transparent, translucent or opaque to permit the wearer to at least partially see through the eye mask 10.

In some embodiments, a control enclosure 20 may have a power jack 31, the power jack 31 configured for receiving a plug of a wall charger 32. In some embodiments, the eye mask 10 may be powered via the wall charger 32, to power the temperature control circuit of the mask and/or to recharge batteries contained within the mask or the control enclosure 20. Wall chargers and connections of wall chargers to enclosures are well understood in the art, wall chargers including AC connections to household power and DC connections to vehicle power, and connections of wall chargers to enclosures including barrel connectors, USB connectors, etc., and all such chargers and connections are contained within the disclosure of this invention.

While preferred and alternative embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. A light-adjustable mask for applying heat and pressure to sinuses, comprising:
   a temperature control circuit layer including at least a plurality of heating wires;
   a weight pocket layer including at least a plurality of user-accessible weight pockets configured for adding at least one of a plurality of weights or a plurality of magnets to weightably apply pressure to the sinuses and weightably retain the plurality of heating wires substantially near sinus regions of a wearer of the light-adjustable mask;
   a memory foam layer configured for contour-molding to a face of the wearer of the light-adjustable mask, the memory foam layer molding to the face of the wearer upon addition of heat via the plurality of heating wires;
   circuitry for thermostatically controlling the plurality of heating wires;

circuitry for controlling duration of heat;
an infrared reflective layer configured for reflecting heat emanating away from the face of the wearer back to the face of the wearer;
a front layer;
an arrangement for permitting the light-adjustable mask to be retained in place on the face of the wearer; and
a power source,
wherein at least the temperature control circuit layer, the weight pocket layer, the memory foam layer, and the infrared reflective layer are affixed to at least form at least a portion of the light-adjustable mask that is (i) shaped to cover sinus regions of the wearer, (ii) shaped to define a recess at a bottom edge of the light-adjustable mask for permitting air to reach a nose of the wearer, and (iii) configured with two apertures facilitating vision through the light-adjustable mask for the wearer; and
wherein the front layer is removably affixable to an outside surface to prevent light from reaching eyes of the wearer, the front layer closing the user-accessible weight pockets upon affixing the front layer to the outside surface.

2. The light-adjustable mask for applying heat and pressure to sinuses of claim 1, wherein the power source is an attached portable battery pack.

3. The light-adjustable mask for applying heat and pressure to sinuses of claim 2, wherein the attached portable battery pack is configured for receiving standard-sized batteries.

4. The light-adjustable mask for applying heat and pressure to sinuses of claim 1, wherein the attached portable battery pack is an attached portable battery pack having rechargeable batteries, wherein the battery pack may be connected to a charger.

5. The light-adjustable mask for applying heat and pressure to sinuses of claim 1, wherein the power source is an alternating current connection to household power.

6. The light-adjustable mask for applying heat and pressure to sinuses of claim 1, wherein the temperature control circuit layer is insulated with at least one layer of insulating material.

7. The light-adjustable mask for applying heat and pressure to sinuses of claim 1, wherein the infrared reflective layer is a biaxially-oriented infrared reflective layer.

8. The light-adjustable mask for applying heat and pressure to sinuses of claim 1, wherein the user-accessible weighted pockets are expandable to accommodate a greater volume of weights or magnets.

9. The light-adjustable mask for applying heat and pressure to sinuses of claim 1, wherein the memory foam layer facilitates application of heat and pressure to a greater portion of the face of the wearer upon the contour-molding to the face of the wearer subsequent to absorption of heat by the memory foam layer from the plurality of heating wires.

10. The light-adjustable mask for applying heat and pressure to sinuses of claim 1, wherein the front layer is at least one of translucent or opaque for enabling the wearer to at least partially see through the front layer.

11. The light-adjustable mask for applying heat and pressure to sinuses of claim 1, wherein the two apertures facilitating vision through the light-adjustable mask are at least one of transparent, translucent, or opaque.

12. The light-adjustable mask for applying heat and pressure to sinuses of claim 1, wherein a layer of the light-adjustable mask adjacent to the face of the wearer includes recesses for eyes of the wearer.

13. The light-adjustable mask for applying heat and pressure to sinuses of claim 1, wherein the wearer can select only on or off settings associated with the plurality of heating wires.

14. The light-adjustable mask for applying heat and pressure to sinuses of claim 1, wherein the wearer can select from multiple temperature settings.

15. The light-adjustable mask for applying heat and pressure to sinuses of claim 1, wherein the circuitry for thermostatically controlling the plurality of heating wires includes at least one temperature sensor to automatically control power to the plurality of heating wires in accordance with a desired temperature.

16. The light-adjustable mask for applying heat and pressure to sinuses of claim 1, wherein the circuitry for controlling duration of heat includes at least a timer that deactivates the plurality of heating wires after a pre-determined time period.

17. The light-adjustable mask for applying heat and pressure to sinuses of claim 1, wherein the memory foam layer is configured for retaining an imprint of facial features of the wearer subsequent to absorption of heat by the memory foam layer from the plurality of heating wires.

18. The light-adjustable mask for applying heat and pressure to sinuses of claim 1, wherein the light-adjustable mask is configured for covering at least the frontal, ethmoid, sphenoid, and maxillary sinus regions of the wearer.

19. The light-adjustable mask for applying heat and pressure to sinuses of claim 1, wherein the arrangement for permitting the light-adjustable mask to be retained in place on the face of the wearer includes at least one elastic strap configured for wrapping around a head of the wearer.

* * * * *